United States Patent
Sybert et al.

(10) Patent No.: US 7,931,692 B2
(45) Date of Patent: Apr. 26, 2011

(54) IMPLANT DERIVED FROM BONE

(75) Inventors: Daryl R. Sybert, New Albany, OH (US); Lawrence A. Shimp, Morganville, NJ (US)

(73) Assignee: Osteotech, Inc.

(*) Notice: Subject to any disclaimer, the term of this patent is extended or adjusted under 35 U.S.C. 154(b) by 838 days.

(21) Appl. No.: 10/468,198

(22) PCT Filed: Feb. 12, 2002

(86) PCT No.: PCT/US02/04131
§ 371 (c)(1), (2), (4) Date: May 25, 2004

(87) PCT Pub. No.: WO02/064181
PCT Pub. Date: Aug. 22, 2002

(65) Prior Publication Data
US 2004/0243242 A1  Dec. 2, 2004

(51) Int. Cl.
A61F 2/44  (2006.01)

(52) U.S. Cl. .................................. 623/23.63

(58) Field of Classification Search ........... 623/17.11, 623/23.61, 23.63, 23.51, 23.57, 16.11, 17.16, 623/919; 8/94.11
See application file for complete search history.

(56) References Cited

U.S. PATENT DOCUMENTS

| | | | |
|---|---|---|---|
| 4,627,853 A | 12/1986 | Campbell et al. | |
| 4,678,470 A | 7/1987 | Nashef et al. | |
| 5,053,049 A | 10/1991 | Campbell | |
| 5,298,254 A | 3/1994 | Prewett et al. | |
| 5,641,518 A | 6/1997 | Badylak et al. | |
| 5,976,186 A | 11/1999 | Bao et al. | |
| 6,090,998 A | 7/2000 | Grooms et al. | |
| 6,123,731 A | 9/2000 | Boyce et al. | |
| 6,432,436 B1 | 8/2002 | Gertzman et al. | |
| 6,569,168 B2 | 5/2003 | Lin | |
| 6,666,866 B2 | 12/2003 | Martz et al. | |
| 6,746,454 B2 | 6/2004 | Winterbottom et al. | |
| 6,911,045 B2 | 6/2005 | Shimp | |
| 7,662,184 B2 | 2/2010 | Edwards et al. | |
| 2003/0130667 A1 | 7/2003 | Lin | |
| 2003/0144743 A1* | 7/2003 | Edwards et al. | 623/23.63 |
| 2004/0098129 A1 | 5/2004 | Lin | |
| 2004/0162562 A1 | 8/2004 | Martz | |
| 2004/0243242 A1* | 12/2004 | Sybert et al. | 623/17.16 |
| 2004/0249377 A1 | 12/2004 | Kaes et al. | |
| 2005/0038511 A1 | 2/2005 | Martz et al. | |
| 2005/0240188 A1 | 10/2005 | Chow et al. | |
| 2005/0251146 A1 | 11/2005 | Martz et al. | |
| 2006/0095043 A1 | 5/2006 | Martz et al. | |
| 2006/0149376 A1 | 7/2006 | Shimp et al. | |
| 2007/0073293 A1 | 3/2007 | Martz et al. | |

FOREIGN PATENT DOCUMENTS

| | | | |
|---|---|---|---|
| WO | 99/38453 | | 8/1999 |
| WO | WO 00/35511 | * | 6/2000 |
| WO | 00/40179 | | 7/2000 |
| WO | 00/50102 | | 8/2000 |

OTHER PUBLICATIONS

Lewandrowski, Kai-Uwe et al. "Kinetics of cortical bone demineralization: Controlled demineralization—a new method for modifying cortical bone allografts," *Journal of Biomedical Materials Research*, vol. 31, pp. 365-372 (1996).

Lewandrowski, Kai-Uwe et al. "Mechanical Properties of Perforated and Partially Demineralized Bone Grafts," *Clinical Orthopaedics and Related Research*, vol. 353, pp. 238-246 (Aug. 1998).

Lewandrowski, Kai-Uwe et al. "An Electron Microscopic Study on the Process of Acid Demineralization of Cortical Bone," *Calcif. Tissue Int.*, vol. 61, pp. 294-297 (1997).

Lewandrowski, Kai-Uwe et al. "Flexural Rigidity in Partially Demineralized Diaphyseal Bone Grafts," *Clinical Orthopaedics and Related Research*, vol. 317, pp. 254-262 (Aug. 1995).

Lewandrowski, Kai-Uwe et al. "Improved Osteoinduction of Cortical Bone Allografts: A Study of the Effects of Laser Perforation and Partial Demineralization," *Journal of Orthopaedic Research*, vol. 15, No. 5, pp. 748-756 (1997).

Urist, Marshall R. "Surface-Decalcified Allogeneic Bone (SDAB) Implants: A Preliminary Report of 10 Cases and 25 Comparable Operations with Undecalcified Lyophilized Bone Implants," *Clinical Orthopaedics and Related Research*, vol. 56, pp. 37-50 (1968).

* cited by examiner

Primary Examiner — Eduardo C Robert
Assistant Examiner — David Comstock

(57) ABSTRACT

An implant which is particularly suitable for the repair and/or replacement of a skeletal joint, e.g., a vertebral joint, includes a unit of monolithic bone possessing at least one demineralized region exhibiting properties of flexibility and resilience, the demineralized region having diminished or insignificant capacity for promoting new bone growth.

41 Claims, No Drawings

IMPLANT DERIVED FROM BONE

BACKGROUND OF THE INVENTION

1. Field of the Invention

This invention relates to an implant fabricated from bone. More particularly, the present invention relates to a stable, yet flexible, prosthetic implant having little if any capacity for promoting new bone growth that could result in the unwanted fusion of bone structures at the implantation site.

2. Description of the Related Art

The vertebral column (spine) is a biomechanical structure composed of a series of joints known as motion segment units. Each motion segment unit includes two adjacent vertebrae and their facet capsules, the intervertebral disc, and connecting ligament tissue. The spine is divided into four major regions which include the cervical, thoracic, lumbar, and sacral regions and functions to protect the spinal cord and nerve roots and provide support to the body.

The intervertebral disc is a fibro-cartilaginous structure located between the two end plates of adjacent vertebrae and is composed of the nucleus pulposus (a gel-like ball located at the center of the disc) and the annulus fibrous (collagen fibers surrounding the nucleus pulposus). The intervertebral disc separates, cushions, and stabilizes the spine providing the spine with resiliency and the ability to withstand compression, rotation, and bending strain. Various types of spinal disorders are known and include kyphosis (backward curvature of the spine), spondylolysis, spondylolisthesis (forward displacement of lumbar vertebrae), scoliosis (abnormal curvature of the spine), and disorders involving ruptured, slipped, damaged and diseased discs, damaged vertebrae, and the like. Patients suffering from the aforementioned disorders typically experience severe pain, numbness, decreased mobility, muscle weakness, and nerve damage and may be treated by surgical removal of the discs. Removal of the discs may then require fusion of the bony elements of the spine.

Spinal fusion can be accomplished within the disc space, anteriorly between adjacent vertebral bodies and/or posteriorly between consecutive processes, e.g., transverse processes, laminae or other posterior elements of the vertebrae. One frequently used spinal fusion technique involves removal of the intervertebral disc and insertion of an anterior supporting structure, e.g., bone grafts, bone substitutes, plugs, bone dowels, cages, and the like, into the intervertebral disc space to prevent collapse of the disc space and promote fusion of the adjacent vertebrae. Unfortunately, this procedure virtually precludes any degree of spinal flexibility.

Other diseases of the spinal joints also require new methods of treatment. For example, the present treatment of lumbar disc herniation provides a compromised functional recovery at best. The disc that has come out of its place has no physiological function and at this time no method is known that will bring back the functional lumbar disc. Fusion is unable to preserve the natural structure and function of the spine. Therefore, a disc prosthesis is needed which can be applied to the disc space and provide the cushioning effect for the disc that is expected of the normal disc.

Several unacceptable attempts have been made to solve this problem such as applying spring loaded disc prosthesis or saline injectable discs with suction cups on the surfaces. The spring loaded disc is so bulky it cannot be inserted into the disc space through the limited opening that is available for this kind of surgery. The saline injectable disc is unstable and the suction cups do not hold it onto the vertebral bodies which have irregular spiky surfaces. While various artificial polymers have been proposed for use as a disc segment, these tend not to have the right biological properties to provide biological attachment to adjacent vertebras or to encourage growth of a supplementary fibrous tissue matrix.

U.S. Pat. No. 4,309,777 describes an artificial disc having a plurality of springs positioned between lower and upper disc portions. In addition, a plurality of spikes extends from the upper and lower portions of the disc to engage the vertebrae. U.S. Pat. No. 4,759,769 describes an artificial spinal disc comprising upper and lower portions connected by both hinge and spring devices. The discs of U.S. Pat. Nos. 4,309,777 and 4,759,769, while stable, lack a physiological structure which probably accounts for their apparent lack of acceptance by the medical community.

U.S. Pat. No. 4,834,757 describes vertebral implant plugs or blocks that are useful in fusing together adjoining vertebral bodies. Once fusion has occurred, articulation of the vertebral joint is no longer possible.

U.S. Pat. No. 4,863,476 describes a spinal implant intended for insertion in an intervertebral space. However, the implant lacks the ability to maintain full contact with the vertebral surfaces.

U.S. Pat. No. 4,863,477 describes a synthetic intervertebral disc prosthesis composed of a rubber-type material having a hollow interior. The interior may be filled with fluid imparting a certain degree of resiliency to the prosthesis. One disadvantage of the prosthesis, however, is that in the anatomical context of the intervertebral space, its design provides very little stability.

A need continues to exist for a truly stable yet fully flexible prosthetic implant that better preserves the natural structure and function of skeletal joints such as the vertebral joints.

It is an object of the invention to provide an implant fabricated from bone, one which is both flexible and resilient and capable of bearing mechanical loads while possessing little if any capacity for promoting new bone growth that could result in the unwanted fusion of bone structures with which the implant comes into contact following its implantation.

It is a particular object of the invention to provide an implant useful in the repair or replacement of skeletal joints.

It is a further object of the invention to provide a replacement intervertebral disc which does not cause the fusion of adjacent vertebrae following its implantation.

SUMMARY OF THE INVENTION

In keeping with these and related objects of the invention, there is provided an implant which comprises a unit of monolithic bone possessing at least one demineralized region exhibiting properties of flexibility and resilience, the demineralized region having diminished or insignificant capacity for promoting new bone growth.

The implant of this invention is particularly suitable for the repair and/or replacement of skeletal joints, e.g., vertebral joints, where its mechanical properties of flexibility and resilience are advantageously utilized and its diminished or insignificant capacity for promoting new bone growth precludes the formation of new bone tissue which would otherwise result in unwanted fusion of adjacent bone structures.

DETAILED DESCRIPTION OF THE PREFERRED EMBODIMENTS

The implant of the invention is preferably a substantially monolithic unit or section of bone sized appropriately for the repair or replacement of a skeletal joint, e.g., an intervertebral disc. At least one region up to and including the entire implant has been demineralized in order to impart flexibility and resilience to the implant and the implant has been further treated in order to diminish or suppress the new bone growth-promoting capacity of the untreated demineralized bone. The multistep process for producing the prosthetic implant of this invention is described below.

The expressions "implant" and "prosthetic implant" as used herein contemplate devices for the replacement of entire skeletal components such as intervertebral discs as well as portions of skeletal components and also includes devices for augmenting existing bone structures.

The expression "monolithic bone" as utilized herein refers to relatively large pieces of human or animal bone, i.e., pieces of bone, autograft, allograft or xenograft, that are of such dimensions as to be capable of withstanding the sort of mechanical loads to which functioning bone structures are typically subjected. The monolithic bone of this invention is to be distinguished from particles, filaments, threads, etc. as disclosed in U.S. Pat. Nos. 5,073,373, 5,314,476 and 5,507,813, which, due to their relatively small dimensions, are incapable of sustaining significant mechanical loads, either individually or in the aggregate. The monolithic bone can be provided as a single integral piece, or unit, of bone or as a piece of bone permanently assembled from a number of smaller bone elements, e.g., as disclosed and claimed in U.S. Pat. No. 5,899,939 the contents of which are incorporated by reference herein.

The term "demineralized" as used herein refers to bone that has been treated such that some of its original mineral content has been removed. Such bone can be treated so that it has a relatively uniform mineral content or it can be treated such that only a region, or portion, of the bone has had its original mineral content removed, e.g., as would be the case with surface demineralization, segmental demineralization, etc. Therefore, the term "demineralized" applies to any bone element or region thereof having less than its full original mineral content.

The term "flexibility" as applied to the demineralized region(s) of the bone-based implant of this invention refers to the characteristic ability, tendency or capacity of the demineralized region(s) of the implant to accommodate, absorb or withstand bending, twisting or torsional forces applied to said region(s), said ability, tendency or capacity being commensurate with the extent and degree of demineralization of the demineralized region(s).

The term "resilience" as applied to the demineralized region(s) of the bone-based implant of this invention refers to the characteristic ability, tendency or capacity of the surface(s) of the demineralized region(s) of the implant to accept, or be conformed to, the shape of impressed surface(s), said ability, tendency or capacity being commensurate with the extent and degree of demineralization of the demineralized region(s).

The implant of this invention comprises a unit of demineralized monolithic bone which has been further treated to reduce, suppress or eliminate its capacity for promoting new bone growth. The bone is preferably chosen to be a section of strong cortical bone such as that obtained from the femur, tibia, fibula, radius, ulna, and the like. The source of the bone can be allograft or xenograft with the appropriate cautionary steps known in the art being taken in each case to prevent contamination by pathogenic and/or antigenic agents. The monolithic bone unit is preferably obtained from a section of a long bone shaft (such as the aforementioned femur, tibia, radius, ulna, etc.) and is configured, e.g., by machining (before or after demineralization and/or the deactivation treatment described below) into the size and shape of the desired prosthetic implant.

Demineralization can be carried out by any of the known and conventional demineralization procedures to reduce the mineral content of at least one region of the monolithic bone unit up to and including the entire bone. The demineralized bone is rubbery in feel, which is to say, it possesses properties of flexibility and resilience. In addition, the demineralized monolithic bone unit possesses sufficient strength to support the sort of mechanical loads that are typical of bone.

The monolithic bone can be provided as a single piece or section of whole bone or, as stated above, it can be built up from two or more smaller bone elements ("built-up monolithic bone"), e.g., as disclosed in U.S. Pat. Nos. 5,899,939 and 6,123,731, the contents of which are incorporated by reference herein. In one embodiment of the latter, smaller bone elements, e.g., particles, fibers, etc., can be assembled by any one of several techniques into a monolithic unit, the monolithic unit can be machined into a prosthetic implant of desired configuration and the implant is thereafter treated as described below in order to render at least its exposed surface, or portion thereof, incapable of promoting significant new bone growth. In another embodiment of a built-up monolithic bone unit, partially or fully demineralized bone sections, e.g., in the form of thin-to-thick sheets or slabs, can be treated to reduce or suppress their capacity for promoting new bone growth and a sheet or slab can then be bonded to each of the two major surfaces of a relatively thick, rigid fully mineralized bone section to form a laminate structure with the flexible resilient demineralized sheets or slabs as its outermost components. This laminate structure can be used as such or further shaped as required into the desired implant configuration.

The aforedescribed laminate embodiment can be particularly advantageous where it is desirable to combine the properties of flexibility and resilience possessed by its outer treated demineralized sheet or slab components with the high mechanical strength properties possessed by its inner fully-mineralized bone core component. Thus, e.g., such a laminate configured as an intervertebral disc will possess outer surfaces that remain flexible and resilient and which do not encourage new bone growth that might lead to fusion of the adjacent vertebrae but will also possess the high mechanical strength properties that are characteristic of fully-mineralized bone.

One skilled in the art will readily recognize that numerous other built-up monolithic bone arrangements besides those described above can be fabricated in accordance with the invention.

When the implant of the present invention is formed from a single piece, or section, of bone, the bone can be substantially completely demineralized, i.e., it can be made to contain less than about 5 weight percent of its original mineral content. It will, of course, be appreciated that a substantially completely demineralized bone monolith will possess the maximum degree of flexibility and resilience but, conversely, the lowest degree of mechanical strength. A partially demineralized bone section, e.g., bone containing a uniformly distributed residual mineral content of from about 20 to about 80 weight percent of the original mineral content, will exhibit less flexibility and resilience than a comparable fully-demineralized bone section but will exhibit greater mechanical strength than the latter, a strength which is proportionate to its residual mineral content.

In one embodiment of the single piece monolithic bone implant that is similar to the built-up bone laminate described above, the single bone section can be surface-demineralized or superficially demineralized, either before or after the bone has been shaped into the desired implant configuration, while the interior or core of the bone section retains its original mineral content. Following treatment of the demineralized surface to reduce or suppress its capacity for promoting new bone growth, the ultimate prosthetic implant will possess functional advantages similar to the built-up laminate embodiment, i.e., flexible, resilient outer surfaces and a high mechanical strength core. The mineralized core is especially advantageous in reducing the possibility of collagen fiber separation, which is a common cause of failure of the implant when placed under axial, compressive loading.

Yet another embodiment of the implant herein can be obtained by segmental, or selective, demineralization of one or more regions of a monolithic bone unit, e.g., as described in U.S. Pat. No. 6,090,998, the contents of which are incorporated by reference herein. The demineralized segments of the bone are then treated, as described below, to suppress their bone growth promoting capacity, either before or after the bone has been shaped into the desired implant configuration.

The order of the steps involved in manufacturing the implant of this invention can vary but begins with the selection of allogenic and/or xenogenic bone stock from which the desired implant will be derived. Suitable sources of xenogenic bone include bone that is of bovine, equine, porcine, ovine or caprine origin. A preferred source of xenogenic bone is porcine bone. The selected bone may be large enough that an implant of the desired dimensions can be machined from it in one piece. If the selected bone is of relatively small dimensions, a quantity of such bone can be assembled into a single large piece as in the built-up monolithic bone referred to above. Alternatively, two or more smaller individual prosthetic implants in accordance with the invention can be provided which, after installation at a bone repair or reconstruction site, function as though they were a single implant.

The bone stock is preferably obtained fresh/frozen and the desired section of bone is obtained by any suitable procedure, e.g., cutting with a saw accompanied by frequent rinsing of the bone in a fluid such as distilled water or saline to keep the bone moist and cool (at or below physiological temperatures to prevent denaturation of bone material). Preferably, the bone section is taken from the diaphysis of a long bone. Associated connective tissue (tendons, ligaments and fascia) is removed. Optionally, the bone section can be frozen at this point if further processing is to be deferred to a later time.

Any conventional means of machining hard materials, including the use of drills, saws, grinders, carving tools, and the like, can be used to obtain the desired final prosthetic implant from the bone section. For example, a rough outline of the outer circumference of the implant can be drawn on the bone and this section can be cut from the bone using a saw. Guide markings can be made on the bone section to indicate any depressions, ridges, openings, or other details that may be desired in the final implant. Preferably, the monolithic bone useful in the invention herein is formed by substantially planar parallel crosscuts across the diaphysis of a femur or similar long bone to produce transversal slices approximately 5 to 30 mm in thickness. Such slices are preferably prepared using, for example, a precision electric saw. The bone is cut with suitable irrigation of water or saline to prevent any increase in the temperature of the bone which is above physiologic temperatures. The bone sections can be further processed to remove residual blood and lipid residues.

Demineralization of a section of bone before or after any final shaping into the implant of the invention can be conducted using conventional procedures that are well known in the art, e.g., subjecting the bone section to strong acids such as hydrochloric acid such as described in Reddi et al., *Proc. Nat. Acad. Sci.* 69:1601-5 (1972), the contents of which are incorporated by reference herein. The extent of demineralization is a function of the strength of the acid solution, the size and shape of the bone and the duration of the demineralization treatment. Reference in this regard may be made to Lewandrowski et al., *J. Biomed. Materials Res.* 31:365-372 (1996), the contents of which are incorporated by reference herein.

In a preferred demineralization procedure, the bone section or sections are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Following defatting, the bone is immersed in acid over time to effect its demineralization. Acids which can be employed in this step include inorganic acids such as hydrochloric acid and organic acids such as peracetic acid. Generally, the concentration of inorganic acid utilized to achieve demineralization is from about 0.1 N to about 2 N and more preferably from about 0.2 N to about 1.0 N. The time of exposure to the acid is increased for lower acid concentrations and decreased for the higher acid concentrations. After acid treatment, the bone section(s) is rinsed with sterile water for injection, optionally buffered with a buffering agent to a final predetermined pH and then finally rinsed with water for injection to remove residual amounts of acid and buffering agent or washed with water to remove residual acid and thereby raise the pH.

Once the bone is demineralized, it is treated in order to reduce or suppress its bone growth-promoting capacity. While the bone may still induce or promote the formation of fibrous tissues on its treated surfaces, such surfaces will no longer possess their full capacity for promoting the growth of new bone. Thus, the treatment of the demineralized bone, which can be thought of as a type of deactivation procedure, results in an implant which resists the tendency to cause fusion of existing bone structures with which the applied implant comes into contact. The deactivation procedure can be carried out by a variety of methods, e.g., treatment with a chemical agent, irradiation with a high energy radiation source, thermal treatment, extraction of the bone growth-promoting proteins, and the like.

A preferred deactivation procedure involves contacting the surface of the demineralized region(s) of the bone with a chemical agent that simultaneously cross links collagen fibers which constitute the bulk of demineralized bone, thus stiffening the affected demineralized region(s), and denatures native proteins which play a role in the bone growth promoting process.

Suitable chemical cross-linking agents include those that contain bifunctional or multifunctional reactive groups and which react with functional groups on amino acids such as an epsilon-amine functional group of lysine or hydroxy-lysine, or the carboxyl functional groups of aspartic and glutamic acids. Chemical cross linking agents of this type include: mono- and dialdehydes, including glutaraldehyde and formaldehyde; polyepoxy compounds such as glycerol polyglycidal ethers, polyethylene glycol diglycidal ethers and other polyepoxy and diepoxy glycidal ethers; tanning agents that include polyvalent metallic oxides such as titanium dioxide, chromium dioxide, aluminum dioxide, zirconium salt, as well as organic tannins and other phenolic oxides derived from plants; chemicals for esterification of carboxyl groups followed by reaction with hydrazide to form activated acyl azide functionalities in the collagen; dicyclohexyl carbodiimide and its derivatives as well as other heterobifunctional cross linking agents; hexamethylene diisocyanate; sugars, including glucose will also cross-link proteins such as, e.g., collagen.

Another treatment suitable for reducing the undesirable osteoinductive properties of demineralized bone is to subject the bone to high energy irradiation, e.g., gamma irradiation of sufficient strength and duration, e.g., about 15,000 to >36,000 gray, to denature the osteoinductive proteins present in the demineralized bone. Control of the environment during irradiation, such as having oxygen present, can influence the degree of cross-linking and favor cross-linking over undesirable chain scission that might weaken the ultimate implant.

Yet another treatment method suitable for suppressing the undesirable bone growth-promoting properties of the demineralized bone involves guanadine hydrochloride extraction of the osteoinductive proteins contained in the demineralized region(s) of the bone.

Thermal treatment of the surface of the demineralized region(s) of the bone, e.g., by brief exposure to temperatures high enough to denature the bone growth-promoting proteins, is also an advantageous expedient for accomplishing deactivation of these proteins. In general, temperatures, e.g., on the order of from about 50° to about 90° C. maintained for from about 5 minutes to about 10 hours are suitable for achieving deactivation.

The thus deactivated implant can be further treated by tanning or other means known in the art to reduce the antigenicity of the implant. For example, glutaraldehyde treatment (see U.S. Pat. No. 5,053,049, the contents of which are incorporated by reference herein) can be used for this purpose if it had not been previously used to achieve deactivation of the bone-growth promoting proteins.

As previously indicated, a preferred implant in accordance with the present invention is an intervertebral disc. The disc can be fabricated from one or more substantially fully-demineralized bone units, optionally possessing a gel-like center which approximates the mechanical properties of the nucleus pulposus.

Such gel-like center can be fabricated, e.g., from a hydrogel-forming polymeric gelling agent. Hydrogel-forming polymeric materials of this type are those that, upon contact with liquids such as water or body fluids, imbibe such liquids forming hydrogels. The polymeric gelling agent can be a substantially water-insoluble, slightly crosslinked, partially neutralized, hydrogel-forming polymer material. Such polymer gelling agent can be prepared from polymerizable, unsaturated, acid-containing monomers. Such monomers include the olefinically unsaturated acids and anhydrides which contain at least one carbon-to-carbon olefinic double bond. More specifically, these monomers can be selected from olefinically unsaturated carboxylic acids and acid anhydrides, olefinically unsaturated sulfonic acids and mixtures thereof.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, beta-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, tricarboxy ethylene and maleic acid anhydride.

Olefinically unsaturated sulfonic acid monomers include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

In the hydrogel-forming polymeric gelling agents used herein, the polymeric component formed from unsaturated, acid-containing monomers may be grafted on to other types of polymer moieties such as starch or cellulose.

The polymeric gelling agent can be introduced into a central cavity formed in the prosthetic implant where it will swell in situ as a result of contact with aqueous body fluid or it can be contained within a fluid permeable structure such as a bag which is placed within the central cavity of the implant. The aforementioned central cavity can already be present in the implant if the bone from which the implant has been obtained possesses a cavity, e.g., as would be the case of a diaphysis section of a long bone which includes a portion of the medullary canal. Once the swollen gel has formed, it will contribute to the overall strength of the implant. The type, shape, and amount of polymeric gel-forming material will be selected so that the swollen material does not exert an undesirable pressure on the implant or adjacent tissues.

Materials can be added to the implant of the invention which will enhance fibrous tissue growth. Such materials can be introduced into the implant before its implantation and/or later applied to its surfaces. Examples of such materials are acellular dermal tissue (Alloderm) and small intestine mucosa.

Medically/surgically useful substances which promote healing can also be incorporated in, or associated with, the prosthetic implant of this invention. Useful substances of this kind which can be incorporated into the implant include, e.g., collagen, insoluble collagen derivatives, etc., and soluble solids and/or liquids dissolved therein, e.g., antiviral agents, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin, and gentamicin, etc.; biocidal/biostatic sugars such as dextran, glucose, etc.; amino acids; peptides; vitamins; inorganic elements; co-factors for protein synthesis; endocrine tissue or tissue fragments, synthesizers; enzymes such as collagenase, peptidases, oxidases, etc.; polymer cell scaffolds with parenchymal cells; angiogenic drugs and polymeric carriers containing such drugs; collagen lattices; antigenic agents; cartilage fragments, living cells such as chondrocytes, mesenchymal stem cells; natural extracts; genetically engineered living cells or otherwise modified living cells; tissue transplants; DNA delivered by plasmid or viral vectors; autogenous tissues such as blood, serum, soft tissue, bone marrow, etc.; bioadhesives; fibronectin; transforming growth factor-beta; endothelial cell growth factors; cementum attachment extracts; ketaserin; insulin-like growth factors (IGF-1)(IGF-2); platelet derived growth factors (PDGF); epidermal growth factor (EGF); interleukin; human alphathrombin; fibroblast growth factors; hormones, in particular, human growth hormone, animal growth hormone and growth hormones such as somatotropin; bone digesters; antitumor agents; immuno-suppressants; permeation enhancers, e.g., fatty acid ester such as laureate, myristate and stearate monoesters of polyethylene glycol, enamine derivatives, alpha-keto aldehydes, etc.; and, nucleic acids Suitable methods of incorporating one of the foregoing medically/surgically useful substances include coating, immersion saturation, packing, co-lyophilization wherein the substance is placed on the graft and lyophilized, spraying, injecting into the implant, etc. The amounts of medically/surgically useful substances utilized can vary widely with optimum levels being readily determined in a specific case by routine experimentation.

Those skilled in the art will recognize that the implant of this invention can be configured by any one of several known and conventional shaping techniques into a limitless variety of shapes and sizes for application in a wide variety of skeletal repair/reconstruction procedures. For example, an implant of this invention can be applied to the repair of flexible joint tissues in the hand, elbow, knee, foot, ankle, spine or other anatomical location as desired. Furthermore, the implant of this invention can be applied as a replacement for any of a variety of joints. Methods and implant shapes known in the art for joint replacement (see, for example U.S. Pat. Nos. 4,871,367; Des. 284,099; Des. 277,784; Des. 277,509; 3,886,600; 3,875,594; 3,772,709; 5,484,443; 5,092,896; 5,133,761; 5,405,400; and 4,759,768; the contents of all of which are incorporated by reference herein) can be readily adapted to the use of the prosthetic implant of this invention.

A preferred method of using the implant of the invention as applied to an intervertebral disc used as a replacement for a damaged intervertebral disc requires insertion of the replacement disc in such a manner that it extends between the bony surfaces of adjacent vertebrae. It is also desirable that the inserted implant be capable of forming a biological connection to the adjacent vertebrae in order to stabilize the construct while minimizing or eliminating the need for additional support devices and at the same time create conditions that will encourage the regrowth of a natural, fibrous, load-bearing material that will augment or replace (either partially or fully) the initially inserted implant. If needed, the auxiliary support devices are preferably load sharing to allow natural movement and loading of the disc prosthesis.

For best results, the disc implant should be placed such that the axis of the medullary canal runs parallel to the axis of loading. This ensures that the bone collagen fibers are loaded axially, which provides the strongest load-bearing capacity. The implant, of annular configuration due to the presence of the medullary canal, is preferably kept intact. If a portion is cut away to the point where the medullary canal is breached, the implant may lose some of its strength and stability.

A preferred prosthetic implant fabricated in accordance with the invention will possess a bulk density of at least about 0.7 g/cm$^3$ and a wet compressive strength of at least about 3 MPa. Wet compressive strength is a well known measurement of mechanical strength and refers to the compressive strength of the implant after it has been immersed in physiological saline (water containing 0.9 g NaCl/100 ml water) for a minimum of 12 hours and a maximum of 24 hours.

The invention will be better understood by way of the following example which is intended to illustrate the invention herein but not to limit it in any way whatsoever.

EXAMPLE

This example illustrates the fabrication of intervertebral disc implants according to the invention.

A femoral shaft and a fibula shaft were cleaned of soft tissue and cut into 15 mm long axial cross sections, ten from each bone. The cross sections were placed in a 5 liter plastic beaker and 4 liters of 0.6 N HCl was added to the beaker to initiate the demineralization process. The beaker was covered and allowed to sit. After 24 hours, the acid was replaced with fresh acid and the cross sections allowed to sit for another 24 hours to complete the demineralization process. The acid was then drained off and the cross sections were rinsed with purified water until the pH of the water surrounding the implants was greater than 3.

The demineralized fibular rings were placed inside the medullary canals of the demineralized femoral rings. Half of the fibula and femoral demineralized cross sections assemblies were placed in a 1 liter beaker and covered with a 50 weight percent aqueous solution of glutaraldehyde while the other half of the cross sections were placed in another 1 liter beaker and covered with a 37 weight percent aqueous solution of formaldehyde. The glutaraldehyde and formaldehyde solutions were added in order to concurrently crosslink collagen fibers in the demineralized regions of the cross section assemblies and at the same time denature proteins in these regions which promote new bone growth. The implants were allowed to sit in the beakers for 24 hours whereupon they were removed and rinsed thoroughly with purified water and allowed to air dry.

The compressive strengths of the treated implants were measured by placing them individually between two platens of a mechanical testing machine. The minimum compressive load sustained by any implant, at 4 mm compressive strain, was greater than 1000 pounds.

In view of the foregoing disclosure and examples, in which various embodiments of the implant of this invention are disclosed and described, including the best mode, those skilled in the art will recognize that various modifications on the specifics of the invention disclosed herein come within the scope of the invention.

What is claimed is:

1. An implant which comprises a unit of monolithic bone, wherein the bone is partially demineralized over substantially the entirety of each of its surfaces, such that substantially no portion of the surface is non-demineralized, wherein at least one region of the bone exhibits properties of flexibility and resilience, and wherein at least one region of the bone has diminished or insignificant capacity for promoting new bone growth.

2. The implant of claim 1 wherein the monolithic bone is derived from allogeneic or xenogeneic bone.

3. The implant of claim 1 wherein the monolithic bone is derived from a single piece or section of bone.

4. The implant of claim 3 which is partially and uniformly demineralized.

5. The implant of claim 1 wherein the monolithic bone is assembled from two or more bone pieces or sections.

6. The implant of claim 5 which is partially and uniformly demineralized.

7. The implant of claim 1 which is partially and uniformly demineralized.

8. The implant of claim 1 wherein at least the surface of the demineralized unit of bone lacks any significant quantity of biologically active bone growth-promoting substances.

9. The implant of claim 1 wherein the monolithic bone is derived from the diaphysis of a long bone.

10. The implant of claim 9 configured as an intervertebral disc.

11. The implant of claim 9 wherein the cavity of the intervertebral disc is filled at least in part with a gel-forming polymer or gel derived therefrom.

12. The implant of claim 1 containing at least one substance which enhances fibrous tissue growth.

13. The implant of claim 12 wherein the substance which enhances fibrous tissue growth is acellular dermal tissue and/or small intestine mucosa.

14. The implant of claim 1 containing at least one medically/surgically useful substance.

15. The implant of claim 14 wherein the medically/surgically useful substance is at least one member of the group consisting of collagen, insoluble collagen derivative, antiviral agent, antimicrobial agent, antibiotic, biocidal/biostatic sugar, amino acid, peptide, vitamin, inorganic element, cofactor for protein synthesis, hormone, endocrine tissue or tissue fragment, synthesizer, enzyme, peptidase, oxidase, polymer drug carrier, collagen lattice, antigenic agent, cartilage fragment, living cells, natural extract, modified living cell, tissue transplant, DNA, autogenous tissue, bioadhesive, fibronectin, transforming growth factor-beta, endothelial cell growth factor, cementum attachment extract, ketaserin, insulin-like growth factor, platelet derived growth factor, epidermal growth factor, interleukin, human alphathrombin, fibroblast growth factor, bone digester, antitumor gent, immunosuppressant, permeation enhancer, and nucleic acid.

16. The implant of claim 1 possessing a bulk density of at least about 0.7 g/cm$^3$ and a wet compressive strength of at least about 3 MPa.

17. The implant of claim 16 configured as an intervertebral disc.

18. The implant of claim 17 possessing a cavity filled at least in part with a gel-forming polymer or gel derived therefrom.

19. A method of making an implant which comprises:
(a) providing a unit of monolithic bone;
(b) partially demineralizing the entire bone wherein the bone is partially demineralized over substantially the entirety of each of its surfaces, such that substantially no portion of the surface is non-demineralized;
(c) treating the bone to suppress, diminish, or eliminate the capacity for promoting new growth; and
(d) partially or full configuring the monolithic bone to a predetermined implant shape following step (a), (b), or (c).

20. The method of claim 19 wherein the monolithic bone is derived from allogeneic or xenogeneic bone.

21. The method of claim 19 wherein the monolithic bone is derived from a single piece or section of bone.

22. The method of claim 21 wherein demineralizing step (b) provides a partially and uniformly demineralized monolithic bone unit.

23. The method of claim 19 wherein the monolithic bone is assembled from two or more bone pieces or sections.

24. The method of claim 23 wherein demineralizing step (b) provides a partially and uniformly demineralized monolithic bone unit.

25. The method of claim 19 wherein demineralizing step (b) provides a partially and uniformly demineralized monolithic bone unit.

26. The method of claim 19 wherein the monolithic bone is derived from the diaphysis of a long bone.

27. The method of claim 26 wherein configuring step (d) provides an intervertebral disc.

28. The method of claim 19 wherein treating step (c) utilizes a chemical agent which denatures proteins in the demineralized bone which promote bone growth.

29. The method of claim 28 wherein treating step (c) utilizes a chemical agent which additionally crosslinks collagen fibers present in the demineralized bone.

30. The method of claim 29 wherein the chemical agent is glutaraldyhyde.

31. The method of claim 19 wherein treating step (c) utilizes heat of sufficient intensity and duration to denature proteins in the demineralized bone which promote bone growth.

32. The method of claim 19 wherein treating step (c) utilizes an extractant to remove proteins from the demineralized bone which promote bone growth.

33. The method of claim 19, wherein treating the bone comprises subjecting the bone to high energy irradiation.

34. The method of claim 33 wherein the high energy irradiation occurs in a controlled environment comprising oxygen.

35. An implant which comprises a unit of monolithic bone, wherein the bone is at least partially demineralized over substantially the entirety of each of its surfaces, such that substantially no portion of the surface is non-demineralized, wherein at least one region of the bone exhibits properties of flexibility and resilience, wherein at least one region of the bone has diminished or insignificant capacity for promoting new bone growth, and wherein substantially no portion of the implant is plasticized.

36. The implant of claim 35 wherein the monolithic bone is derived from a single piece or section of bone.

37. The implant of claim 35 wherein the monolithic bone is assembled from two or more bone pieces or sections.

38. The implant of claim 35 wherein the implant is uniformly demineralized.

39. The implant of claim 35 wherein the implant is configured as an intervertebral disc.

40. The implant of claim 35 further comprising at least one substance which enhances fibrous tissue growth.

41. The implant of claim 40 wherein the substance which enhances fibrous tissue growth is acellular dermal tissue and/or small intestine mucosa.

* * * * *